United States Patent [19]

Eicken et al.

[11] 4,340,418
[45] Jul. 20, 1982

[54] HERBICIDAL AGENTS BASED ON N-AZOLYLMETHYLACETANILIDES AND CYCLOHEXANE-1,3-DIONE DERIVATIVES

[75] Inventors: Karl Eicken, Wachenheim; Bruno Wuerzer, Otterstadt, both of Fed. Rep. of Germany

[73] Assignee: BASF Aktiengesellschaft, Fed. Rep. of Germany

[21] Appl. No.: 149,965

[22] Filed: May 15, 1980

[30] Foreign Application Priority Data

May 19, 1979 [DE] Fed. Rep. of Germany ....... 2920300

[51] Int. Cl.$^3$ ............................................. A01N 43/56
[52] U.S. Cl. .......................................... 71/92; 71/98; 71/103
[58] Field of Search ............................ 71/92, 98, 103

[56] References Cited

FOREIGN PATENT DOCUMENTS 2648008 5/1978 Fed. Rep. of Germany .
2744396 7/1978 Fed. Rep. of Germany .
2704281 8/1978 Fed. Rep. of Germany .
2822304 11/1978 Fed. Rep. of Germany .
2742583 4/1979 Fed. Rep. of Germany .

*Primary Examiner*—Catherine L. Mills
*Attorney, Agent, or Firm*—Keil & Witherspoon

[57] ABSTRACT

Herbicidal agents containing an N-azolylmethylhaloacetanilide of the formula

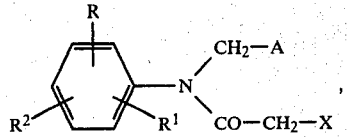

where R, $R^1$, $R^2$, A and X have the meanings given in the disclosure, and a substituted cyclohexane-1,3-dione derivative of the formula

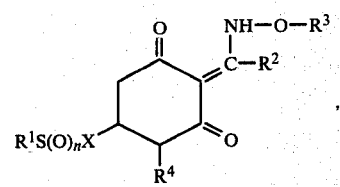

where $R^1$, $R^2$, $R^3$, $R^4$, X and n have the meanings given in the disclosure, or a metal salt or ammonium salt of this cyclohexane-1,3-dione derivative.

The ratio of N-azolylmethylhaloacetanilide of the formula I to cyclohexane-1,3-dione derivative of the formula II is from 1:0.125 to 1:10 parts by weight. The agents are suitable for combating unwanted grassy plants.

4 Claims, No Drawings

HERBICIDAL AGENTS BASED ON N-AZOLYLMETHYLACETANILIDES AND CYCLOHEXANE-1,3-DIONE DERIVATIVES

The present invention relates to herbicidal agents containing mixtures of N-azolylmethylacetanilides and cyclohexane-1,3-dione derivatives, and processes for controlling unwanted plant growth with these agents.

The haloacetanilides, which are disclosed in German Laid-Open Application DE-OS No. 2,648,008 and bear a substituted or unsubstituted azolylmethyl radical which is attached to the nitrogen via a ring nitrogen atom, such as pyrazol-1-yl-methyl, triazol-1-yl-methyl or tetrazol-1-yl-methyl, have an excellent herbicidal action on grasses at low application rates. Further, haloacetanilides having an action on grasses have been disclosed in which the azolylmethyl radical is imidazol-1-yl-methyl (German Laid-Open Applications DE-OS Nos. 2,704,281 and 2,744,396).

It has also been disclosed that cyclohexane-1,3-dione derivatives are particularly effective for combating grassy plants, and are preferably used postemergence (German Laid-Open Application DE-OS No. 2,822,304).

We have found that herbicidal agents containing a mixture of N-azolylmethylhaloacetanilides of the formula

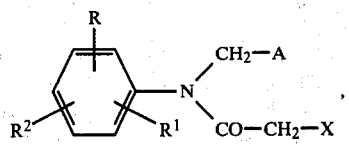

where R denotes hydrogen, linear or branched alkyl or alkoxy of a maximum of 5 carbon atoms, $R^1$ and $R^2$ are identical or different and each denotes hydrogen, halogen, or linear or branched alkyl or alkoxy of a maximum of 5 carbon atoms, R and $R^2$ together denote an ortho-position alkylene chain of a maximum of 6 carbon atoms which is unsubstituted or substituted by linear alkyl of a maximum of 4 carbon atoms, X denotes chlorine or bromine, and A denotes azole attached via a ring nitrogen atom and which is unsubstituted or mono- or poly-substituted by halogen, phenyl, alkyl, alkoxy, alkylthio or perfluoroalkyl, each of a maximum of 4 carbon atoms, cyano, carboxy, carbalkoxy, where alkoxy is of a maximum of 4 carbon atoms, or alkanoyl of a maximum of 4 carbon atoms, or A denotes a salt of an azole containing 2 or 3 nitrogen atoms, and substituted cyclohexane-1,3-dione derivatives of the formula

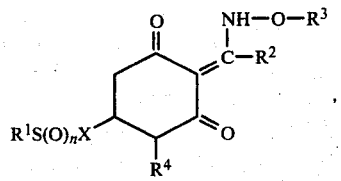

where $R^1$ denotes alkyl of a maximum of 4 carbon atoms, phenyl, or phenyl or benzyl substituted by halogen, alkyl or alkoxy of a maximum of 4 carbon atoms, $R^2$ denotes alkyl of a maximum of 4 carbon atoms, $R^3$ denotes alkyl or alkenyl of a maximum of 4 carbon atoms, $R^4$ denotes hydrogen or alkoxycarbonyl of a maximum of 5 carbon atoms, X denotes linear or branched alkylene of a maximum of 4 carbon atoms, and n denotes one of the integers 0, 1 and 2, or metal salts or ammonium salts of these cyclohexane-1,3-dione derivatives, have a more intensive action on grassy plants than herbicidal agents containing merely an N-azolylmethylacetanilide of the formula I or a cyclohexane-1,3-dione of the formula II. Surprisingly, N-azolylmethylacetanilides of the formula I and cyclohexane-1,3-diones of the formula II exhibit in these mixtures a pronounced synergistic action, especially at application rates at which one or both components have only insufficient action.

Suitable mixture components of the formula I are N-azolylmethylhaloacetanilides in which R is hydrogen, alkyl of a maximum of 5 carbon atoms, such as methyl, ethyl, n-propyl, isopropyl, n-butyl, sec-butyl, isobutyl, tert-butyl, or n-pentyl and branched pentyl, or alkoxy of a maximum of 5 carbon atoms, such as methoxy, ethoxy, propoxy, butoxy, or pentoxy; $R^1$ and $R^2$ are identical or different and each denotes hydrogen, halogen, such as fluorine, chlorine, bromine and iodine, alkyl of a maximum of 5 carbon atoms, such as methyl, ethyl, n-propyl, isopropyl, n-butyl, sec-butyl, isobutyl, tert-butyl, n-pentyl and branched pentyl, or alkoxy of a maximum of 5 carbon atoms, such as methoxy, ethoxy, propoxy, butoxy, or pentoxy; R and $R^2$ together denote an ortho-position alkylene chain of a maximum of 6 carbon atoms which is unsubstituted or substituted by alkyl of a maximum of 4 carbon atoms, such as ethylene, trimethylene, tetramethylene, 1-methyltrimethylene, 1,1-dimethyltrimethylene, and 1,1-dimethyltetramethylene; X denotes chlorine or bromine, preferably chlorine; and A denotes azole attached via a ring nitrogen atom, such as pyrrole, pyrazole, imidazole, 1,2,4-triazole, 1,2,3-triazole and tetrazole, which is unsubstituted or mono- or polysubstituted independently by halogen, phenyl, alkyl, alkoxy, alkylthio or perfluoroalkyl, each of a maximum of 4 carbon atoms, cyano, carboxy, carbalkoxy of a maximum of 4 carbon atoms in the alkoxy, or alkanoyl of a maximum of 4 carbon atoms, such as 2,6-dimethylpyrrole, tetramethylpyrrole, 3(5)-methylpyrazole, 4-methylpyrazole, 3(5)-ethylpyrazole, 4-ethylpyrazole, 3(5)-isopropylpyrazole, 4-isopropylpyrazole, 3,5-dimethylpyrazole, 3,5-dimethyl-4-acetylpyrazole, 3,5-dimethyl-4-propionylpyrazole, 3,4,5-trimethylpyrazole, 3(5)-phenylpyrazole, 4-phenylpyrazole, 3,5-diphenylpyrazole, 3(5)-phenyl-5(3)-methylpyrazole, 3(5)-chloropyrazole, 4-chloropyrazole, 4-bromopyrazole, 4-iodopyrazole, 3,4,5-trichloropyrazole, 3,4,5-tribromopyrazole, 3,5-dimethyl-4-chloropyrazole, 3,5-dimethyl-4-bromopyrazole, 4-chloro-3(5)-methylpyrazole, 4-bromo-3(5)-methylpyrazole, 4-methyl-3,5-dichloropyrazole, 3(5)-methyl-4,5(3)-dichloropyrazole, 3(5)-chloro-5(3)-methylpyrazole, 4-methoxypyrazole, 3(5)-methyl-5(3)-methoxypyrazole, 3(5)-ethoxy-4,5(3)-dimethylpyrazole, 3(5)-methyl-5(3)-trifluoromethylpyrazole, 3,5-bistrifluoromethylpyrazole, 3(5)-methyl-5(3)-carbethoxypyrazole, 3,5-biscarbethoxypyrazole, 3,4,5-triscarbethoxypyrazole, 3(5)-methyl-5(3)-methylthio-4-carbethoxypyrazole, 4-methyl-3,5-biscarbethoxypyrazole, 4-cyanopyrazole, 4-methoxy-3,5-dichloropyrazole, 4,5-dichloroimidazole, 2-methyl-4,5-dichloroimidazole, 2-ethyl-4,5-dichloroimidazole, 3(5)-methyl-1,2,4-triazole, 3,5-dimethyl-1,2,4-triazole, 3(5)-chloro-1,2,4-triazole, 3(5)-bromo-1,2,4-triazole, 3(5)-chloro-5(3)-methyl-1,2,4-triazole, 3,5-dichloro-1,2,4- triazole, 3,5-dibromo-1,2,4-triazole, 3(5)-chloro-5(3)-cyano-1,2,4-triazole, 3(5)-chloro-5(3)-phenyl-1,2,4-triazole, 3(5)-chloro-5(3)-carbomethoxy-1,2,4-triazole, 3(5)-methylthio-1,2,4-triazole, 4(5)-methyl-1,2,3-triazole, 4,5-dimethyl-1,2,3-triazole, 4(5)-phenyl-1,2,3-triazole, 4(5)-chloro-1,2,3-triazole, 1,2,3-triazol-4(5)-ylcarboxylic acid ethyl ester, 1,2,3-triazol-4,5-yl-dicarboxylic acid dimethyl ester, 5-methyltetrazole, 5-chlorotetrazole, and tetrazolyl-5-carboxylic acid ethyl ester.

When the substituted or unsubstituted azole contains 2 or 3 nitrogen atoms, A may also be attached in a saltlike manner to one of the conventional strong inorganic or organic acids, such as hydrochloric acid, hydrobromic acid, nitric acid, sulfuric acid, tetrafluoboric acid, fluosulfonic acid, formic acid, a halogenated carboxylic acid, e.g., trichloroacetic acid, an alkanesulfonic acid, e.g., methanesulfonic acid, a halogenated alkanesulfonic acid, e.g., trifluoromethanesulfonic acid, perfluorohexanesulfonic acid, or an arylsulfonic acid, e.g., dodecylbenzenesulfonic acid.

Preferred acetanilides are those which bear, in the 2- and 6-positions on the phenyl ring, methyl or ethyl and, in the 3-position, hydrogen, methyl or ethyl, suitable azoles being pyrazole, triazoles, or tetrazole, each of which may be substituted by lower alkyl, alkoxy, carbalkoxy, cyano or halogen.

In particular, the herbicidal agents according to the invention contain the following N-azolylmethylhaloacetanilides: 2-chloro-2',6'-dimethyl-N-(pyrazol-1-yl-methyl)-acetanilide, 2-chloro-2'-methyl-6'-ethyl-N-(pyrazol-1-yl-methyl)-acetanilide, 2-chloro-2',6'-dimethyl-N-(4-methylpyrazol-1-yl-methyl)-acetanilide, 2-chloro-2'-methyl-6'-ethyl-N-(4-methoxypyrazol-1-yl-methyl)-acetanilide, 2-chloro-2'-methyl-5'-ethyl-N-(3(5)-methylpyrazol-1-yl)-acetanilide, 2-chloro-2',6'-dimethyl-N-(3,5-dimethylpyrazol-1-yl-methyl)-acetanilide, 2-chloro-2',6'-dimethyl-N-(1,2,4-triazol-1-yl-methyl)-acetanilide, 2-chloro-2',6'-dimethyl-N-(4-chloropyrazol-1-yl-methyl)-acetanilide, 2-chloro-2',3',6'-trimethyl-N-(pyrazol-1-yl-methyl)-acetanilide, 2-chloro-2'-methyl-6'-ethyl-N-(3,5-dimethyl-pyrazol-1-yl-methyl)-acetanilide, 2-chloro-2',6'-diethyl-N-(3,5-dimethyl-pyrazol-1-yl-methyl)-acetanilide, 2-chloro-2',3',6'-trimethyl-N-(3,5-dimethyl-pyrazol-1-yl-methyl)-acetanilide, 2-chloro-2',6'-diethyl-N-(4-methylpyrazol-1-yl-methyl)-acetanilide, 2-chloro-2'-methyl-6'-ethyl-N-(4-methylpyrazol-1-yl-methyl)-acetanilide, 2-chloro-2',3',6'-trimethyl-N-(4-methylpyrazol-1-yl-methyl)-acetanilide, 2-chloro-2',6'-dimethyl-N-(3-(5)-methyl-pyrazol-1-yl-methyl)-acetanilide, 2-chloro-2',6'-diethyl-N-(3-(5)-methylpyrazol-1-yl-methyl)-acetanilide, 2-chloro-2',6'-dimethyl-N-(4-methoxypyrazol-1-yl-methyl)-acetanilide, 2-chloro-2',6'-diethyl-N-(pyrazol-1-yl-methyl)-acetanilide, 2-chloro-2'-methyl-6'-ethyl-N-(1,2,4-triazol-1-yl-methyl)-acetanilide, 2-chloro-2',6'-diethyl-N-(1,2,4-triazol-1-yl-methyl)-acetanilide, 2-chloro-2',3',6'-trimethyl-N-(1,2,4-triazol-1-yl-methyl)-acetanilide, 2-bromo-2',6'-dimethyl-N-(pyrazol-1-yl-methyl)-acetanilide and 2-bromo-2'-methyl-6'-ethyl-N-(pyrazol-1-yl-methyl)-acetanilide.

Suitable mixture components of the formula II are for example cyclohexane-1,3-dione derivatives in which $R^1$ is alkyl of a maximum of 4 carbon atoms, such as methyl, ethyl, n-propyl, isopropyl, n-butyl, phenyl, or phenyl or benzyl substituted by halogen, alkyl or alkoxy of a maximum of 4 carbon atoms, such as 4-chlorophenyl, 2-methylphenyl, 3-methylphenyl, 4-methylphenyl, 2,5-dimethylphenyl, 2,4-dichlorophenyl and 4-methoxyphenyl; $R^2$ denotes alkyl of a maximum of 4 carbon atoms, such as methyl, ethyl, n-propyl and n-butyl; $R^3$ denotes alkyl or alkenyl of a maximum of 4 carbon atoms, such as ethyl and allyl; $R^4$ denotes hydrogen or alkoxycarbonyl of a maximum of 5 carbon atoms, such as methoxycarbonyl and ethoxycarbonyl; X denotes alkylene of a maximum of 4 carbon atoms, such as methylene, ethylene, methylethylene or ethylmethylene; and n denotes one of the integers 0, 1 and 2. The compounds may also be in the form of metal or ammonium salts, e.g., alkali metal or alkaline earth metal salts, such as sodium, potassium, calcium or barium salts, as manganese, copper, zinc, cobalt, iron or silver salts, or as tetrabutylammonium, trimethylbutylammonium or dimethylbenzylhexadecylammonium salts.

Preferred mixture components of the formula II are those in which $R^1$ is alkyl of 1 to 3 carbon atoms, phenyl, or phenyl substituted by chlorine, methyl or methoxy, $R^2$ is alkyl of 2 or 3 carbon atoms, $R^3$ is ethyl or allyl, $R^4$ is hydrogen, and X is linear or branched alkylene of 1 to 3 carbon atoms.

The ratio of the components to each other may vary widely; the ratio selected depends first and foremost on the spectrum of weeds and grasses to be combated, and possibly also on the development stage of the plants to be combated. The ratio of N-azolylmethylhaloacetanilide of the formula I to cyclohexane-1,3-dione derivative of the formula II is preferably from 1:0.125 to 1:10 parts by weight.

The amount of pure active ingredient mixture in the herbicidal agents according to the invention which is necessary for combating unwanted plant growth depends on the type of soil, the composition of the stand, and the climatic conditions prevailing where the agents are to be used. Generally, application rates are from 0.1 to 5 kg of active ingredient mixture per hectare.

Crops in which the herbicidal agents according to the invention may be used are essentially those in which the individual components may be employed, e.g., rape and other cabbage varieties, groundnuts, cotton, potatoes (Irish potatoes), sugarbeets, soybeans, established alfalfa, strawberries and numerous other, annual or perennial, herbaceous or woody crop plants.

The application method employed is of importance here. The agents according to the invention may be applied either pre- or postemergence in crop and unwanted plants. Further, a special application technique is also suitable in which the spray is directed in such a manner that the leaves of the crop plants come as little as possible into contact with the agents, and the unwanted plants growing among or below them, or the soil are contacted (post-directed, lay-by).

In view of the many application methods possible, the agents according to the invention, or compositions containing them, may be used in a large number of crops for removing unwanted plant growth.

The following crop plants may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| Beta vulgaris spp. altissima | sugarbeets |
| Beta vulgaris spp. rapa | fodder beets |
| Beta vulgaris spp. esculenta | table beets, red beets |

-continued

| Botanical name | Common name |
| --- | --- |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phasedus lunatus | limabeans |
| Phaseolus mungo | mungbeans |
| Phaseolus vulgaris | snapbeans, green beans, |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | |
| Ricinus communis | |
| Saccharum officinarum | sugar cane |
| Sesamum indicum | sesame |
| Solanum tuberosum | Irish potatoes |
| Sorghum bicolor (s. vulgare) | grain sorghum |
| Sorghum dochna | |
| Spinacia oleracea | spinach |
| Theobroma cacao | cacao plants |
| Trifolium pratense | red clover |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

The herbicidal agents according to the invention are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient mixture.

Examples of formulations are given below.

I. 20 parts by weight of a mixture of 1 part by weight of 2-chloro-2',6'-dimethyl-N-(pyrazol-1-yl-methyl)-acetanilide and 2 parts by weight of 2-(1-ethoxyaminobutylidene)-5-(2-ethylthiopropyl)-cyclohexane-1,3-dione is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient mixture.

II. 20 parts by weight of a mixture of 1 part by weight of 2-chloro-2',6'-dimethyl-N-(pyrazol-1-yl-methyl)-acetanilide and 4 parts by weight of 2-(1-ethoxyaminobutylidene)-5-(2-ethylthiopropyl)-cyclohexane-1,3-dione is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient mixture.

III. 3 parts by weight of a mixture of 1 part by weight of 2-chloro-2',6'-dimethyl-N-(pyrazol-1-yl-methyl)-acetanilide and 1 part by weight of 2-(1-ethoxyaminobutylidene)-5-(2-ethylthiopropyl)-cyclohexane-1,3-dione is intimately mixed with 97 parts by weight of particulate kaolin. A dust is obtained containing 3% by weight of the active ingredient mixture.

IV. 20 parts by weight of a mixture of 4 parts by weight of 2-chloro-2',6'-dimethyl-N-(pyrazol-1-yl-methyl)-acetanilide and 1 part by weight of 2-(1-ethoxyaminobutylidene)-5-(2-ethylthiopropyl-cyclohexane-1,3-dione is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

V. 30 parts by weight of a mixture of 1 part by weight of 2-chloro-2',6'-dimethyl-N-(pyrazol-1-yl-methyl)-acetanilide and 4 parts by weight of 2-(1-ethoxyaminobutylidene)-5-(2-ethylthiopropyl)-cyclohexane-1,3-dione is intimately mixed with a mixture consisting of 92 parts by weight of powdered silica gel and 8 parts by weight of paraffin oil which has been sprayed onto the surface of this silica gel. A formulation of the active ingredient mixture is obtained having good adherence.

The new herbicidal active ingredients according to the invention may be mixed and applied together with numerous representatives of other herbicidal or growth-regulating active ingredient groups. Examples of suitable mixture components are diazines, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, etc. Such combinations broaden the spectrum of action. A number of active ingredients which, when combined with the new compounds, give mixtures useful for widely varying applications are given below by way of example:

5-amino-4-chloro-2-phenyl-3(2$\underline{H}$)-pyridazinone
5-amino-4-bromo-2-phenyl-3(2$\underline{H}$)-pyridazinone
5-amino-4-chloro-2-cyclohexyl-3(2$\underline{H}$)-pyridazinone
5-amino-4-bromo-2-cyclohexyl-3(2$\underline{H}$)-pyridazinone
5-methylamino-4-chloro-2-(3-trifluoromethylphenyl)-3(2$\underline{H}$)-pyridazinone
5-methylamino-4-chloro-2-(3-$\alpha,\alpha,\beta,\beta$-tetrafluoroethoxyphenyl)-3-(2$\underline{H}$)-pyridazinone
5-dimethylamino-4-chloro-2-phenyl-3(2$\underline{H}$)-pyridazinone
4,5-dimethoxy-2-phenyl-3(2$\underline{H}$)-pyridazinone
4,5-dimethoxy-2-cyclohexyl-3(2$\underline{H}$)-pyridazinone
4,5-dimethoxy-2-(3-trifluoromethylphenyl)-3(2$\underline{H}$)-pyridazinone
5-methoxy-4-chloro-2-(3-trifluoromethylphenyl)-3(2$\underline{H}$)-pyridazinone
5-amino-4-bromo-2(3-methylphenyl)-3(2$\underline{H}$)-pyridazinone
3-(1-methylethyl)-1H-2,1,3-benzothiadiazin-4(3$\underline{H}$)-one-2,2-dioxide and salts
3-(1-methylethyl)-8-chloro-1H-2,1,3-benzothiadiazin-4(3$\underline{H}$)-one-2,2-dioxide and salts
3-(1-methylethyl)-8-fluoro-1H-2,1,3-benzothiadiazin-4(3$\underline{H}$)-one-2,2-dioxide and salts
3-(1-methylethyl)-8-methyl-1H-2,1,3-benzothiadiazin-4(3$\underline{H}$)-one-2,2-dioxide and salts
1-methoxymethyl-3-(1-methylethyl)-2,1,3-benzothiadiazin-4(3$\underline{H}$)-one-2,2-dioxide
1-methoxymethyl-8-chloro-3-(1-methylethyl)-2,1,3-benzothiadiazin-4(3$\underline{H}$)-one-2,2-dioxide
1-methoxymethyl-8-fluoro-3-(1-methylethyl)-2,1,3-benzothiadiazin-4(3$\underline{H}$)-one-2,2-dioxide
1-cyano-8-chloro-3-(1-methylethyl)-2,1,3-benzothiadiazin-4(3$\underline{H}$)-one-2,2-dioxide
1-cyano-8-fluoro-3-(1-methylethyl)-2,1,3-benzothiadiazin-4(3$\underline{H}$)-one-2,2-dioxide
1-cyano-8-methyl-3-(1-methylethyl)-2,1,3-benzothiadiazin-4(3$\underline{H}$)-one-2,2-dioxide
1-cyano-3-(1-methylethyl)-2,1,3-benzothiadiazin-4(3$\underline{H}$)-one-2,2-dioxide
1-azidomethyl-3-(1-methylethyl)-2,1,3-benzothiadiazin-4(3$\underline{H}$)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-$\beta$-chloroethyl-2,6-dinitro-4-trifluoromethylaniline
N-n-propyl-N-cyclopropylmethyl-2,6-dinitro-4-trifluoromethylaniline
N-bis-(n-propyl)-2,8-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-($\beta$-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.-butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate 4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenylcarbamate
ethyl N-3-(2'-methylphenoxycarbonylamino)-phenylcarbamate
methyl N-3-(4'-fluorophenoxycarbonylamino)-phenylthiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiocarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate 3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium-3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione 2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloro-acetanilide
2-methyl-6-ethyl-N-(pyrazol-1-yl-methyl)-2-chloroacetanilide
2,6-dimethyl-N-(pyrazon-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2-(2-methyl-4-chlorophenoxy-N-methoxyacetamide
2-(α-naphthoxy)-N,N-diethylpropionamide
2,2-diphenyl-N,N-dimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
N-2,4-dimethyl-5-(trifluoromethyl)-sulfonylaminophenylacetamide
N-4-methyl-5-(trifluoromethyl)-sulfonylaminophenylacetamide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,0,$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea 1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl α-naphthoxyacetate
2-(2-methylphenoxy)-propionic acid (salts, esters, amides)
2-(4-chlorophenoxy)-propionic acid (salts, esters, amides) 2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phosphorodithionate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
sodium chlorate
ammonium thiocyanate
calcium cyanamide.

It may also be useful to apply the mixtures according to the invention in admixture with other crop protection agents, e.g., agents for combating pests or phytopathogenic fungi or bacteria. The compounds may also be mixed with solutions of mineral matters used to remedy nutritional or trace element deficiencies. To initiate the herbicidal action, wetting agents, spreader-stickers and non-phytotoxic oils and oil concentrates may be added.

The following greenhouse experiments and experiments in the open illustrate the synergistic increase in action achieved by the combined use of N-azolylmethylacetanilides of the formula I and cyclohexane-1,3-dione derivatives of the formula II in the herbicidal agents according to the invention.

The vessels employed were plastic flowerpots having a volume of 300 cm$^3$, and which were filled with a sandy loam containing about 1.5% humus. The seeds of the test plants (cf. Table 1) were sown shallow, and separately, according to species. For the preemergence treatment, the active ingredients were applied to the surface of the soil immediately after the seeds had been sown. The individual active ingredients and mixtures thereof were emulsified or suspended in water as vehicle, and sprayed through finely distributing nozzles. After the agents had been applied, the vessels were lightly sprinkler-irrigated to induce germination and growth and to activate the chemical agents. Transparent plastic covers were than placed on the vessels until the plants had taken root. The cover ensured uniform germination of the plants, insofar as this was not impaired by the chemicals, and prevented readily volatile active ingredients from evaporating. The pots were set up in the greenhouse—species from warmer areas at from 25° to 40° C., and species from moderate climates at 15° to 30° C. The experiments were run for from 4 to 6 weeks. During this period, the plants were tended and their reactions to the various treatments assessed.

In the experiments in the open, the agents were emulsified or suspended in water as vehicle, and applied, with the aid of a motor-driven plot spray mounted on a tractor, to small plots of loamy sand and loam of pH 5 to 6 and containing from 1 to 1.5% humus. The crop plant selected was sugarbeet. To combat broadleaved weeds, a treatment was initially carried out, after sowing and before emergence of the crop and unwanted plants, with from 2.0 to 2.5 kg of the herbicide 1-phenyl- 4-amino-5-chloropyridazone-(6) per hectare instead of mechanical weeding. Eight weeks later, a second spraying was effected postemergence with the agents according to the invention, which is predominantly to control unwanted grasses. The development stages of the unwanted grasses ranged from still ungerminated seed in the soil to tillered plants unaffected by chloridazon.

Where no rain fell, the plots were initially sprinkled to ensure normal growth of crop and unwanted plants. The experiments were run for several months.

The following tables containing the compounds investigated, the application rates in kg/ha of active ingredient, and the plants used for the tests. The scale used for assessment was 0 to 100, 0 denoting no damage or normal emergence, and 100 denoting nonemergence or complete destruction of at least the visible plant parts.

The following active ingredients were used:
2-chloro-2',6'-dimethyl-N-(pyrazol-1-yl-methyl)-acetanilide (active ingredient A)
2-(1-ethoxyaminobutylidene)-5-(2-ethylthiopropyl)-cyclohexane-1,3-dione and its Na salt (active ingredient B)

To check the synergistic action arithmetically, the action of the individual compounds at varying application rates was first ascertained (dosage-action series). From these figures, the action theoretically to be expected when two components with a known action are mixed was then calculated by the method suggested by F. H. A. Rummens in Weed Science, 23, 4 et seq., 1975. These calculated figures were then compared with the results actually obtained in the experiments for the mixtures. If the degree of damage recorded is greater than that calculated, the action is synergistic.

Results

The figures in Table 2 show that the degree of damage actually found in the grassy plants given by way of example exceeds that theoretically to be expected. These active ingredient combinations therefore have a synergistic action which goes beyond a purely additive action of the individual components.

TABLE 1

| Botanical name | Abbreviation in tables | Common name |
| --- | --- | --- |
| Alopecurus myosuroides | Alopec. myosur. | slender foxtail |
| Beta vulgaris | — | sugarbeets |
| Brachiaria platyphylla | Brachiaria plat. | broadleaf signalgrass |
| Echinochloa crus-galli | Echinochl. c.g. | barnyardgrass |
| Hordeum vulgare | Hord. vulgare | barley |
| Rottboellia exaltata | Rottboellia ex. | itchgrass |

TABLE 2

Synergistic herbicidal action of mixtures of A and B; preemergence treatment in the greenhouse

| Active ingredient | Appln. rate [kg/ha] | Alopec. myosur. damage [%] calc.+ | found++ | Brachiaria plat. damage [%] calc.+ | found++ | Rottboellia ex. damage [%] calc.+ | found++ | Hord. vulgare damage [%] calc.+ | found++ |
| --- | --- | --- | --- | --- | --- | --- | --- | --- | --- |
| A + B | 0.06 + 0.06 | 83 | 98 | 76 | 92 | 24 | 58 | 72 | 95 |
|  | 0.125 + 0.125 | 89 | 100 | 89 | 98 | 33 | 68 | 95 | 99 |
|  | 0.25 + 0.25 | 93 | 100 | 95 | 98 | 41 | 72 | 99 | 99 |
|  | 0.125 + 0.03 | 86 | 98 | 75 | 82 | 20 | 45 | 89 | 97 |
|  | 0.06 + 0.25 | 92 | 98 | 87 | 95 | 28 | 50 | 97 | 97 |

+theoretically calculated
++found

TABLE 3

Control of unwanted grasses in sugarbeets by synergistic action of mixtures of A and B; postemergence treatment in the open

| Active ingredient | Appln. rate [kg/ha] | Beta vulgaris | Alopec. myosur. | Echinochl. |
| --- | --- | --- | --- | --- |
| A | 0.5 | 0 | 22 | 45 |
|  | 1.0 | 0 | 48 | 52 |
|  | 2.0 | 2 | 66 | 72 |
| B | 0.5 | 0 | 71 | 87 |
|  | 1.0 | 3 | 84 | 82 |
| A + B | 1.0 + 0.25 | 0 | 89 | 95 |
|  | 1.0 + 0.5 | 0 | 95 | 100 |

0 = no damage
100 = plants destroyed

We claim:

1. A herbicidal agent comprising a herbicidally effective amount of a mixture of an N-azolylmethylhaloacetanilide of the formula

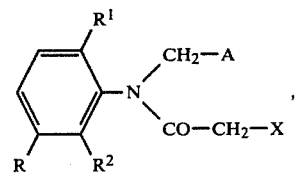

where R is hydrogen, $R^1$ and $R^2$ are identical or different and each is methyl or ethyl, X is chlorine and A is pyrazol-1-yl, and the substituted cyclohexane-1,3-dione derivative 2-(1-ethoxyaminobutylidene)-5-(2-ethylthiopropyl)-cyclohexane-1,3-dione the ratio of N-azolylmethylhaloacetanilide to cyclohexane-1,3-dione being from 1:0.125 to 1:10 parts by weight.

2. The herbicidal agent of claim 1, wherein the N-azolylmethylhaloacetanilide of the formula I is 2-chloro-2',6'-dimethyl-N-(pyrazol-1-yl-methyl)-acetanilide.

3. The herbicidal agent of claim 2, wherein the ratio of N-azolylmethylhaloacetanilide to cyclohexane-1,3-dione is from 12.5:3 to 3:12.5 parts by weight.

4. A process for combating unwanted plant growth, wherein the plants or the soil are treated with a herbicidally effective amount of a herbicidal agent as set forth in claim 1.

* * * * *